US00PP13313P2

(12) United States Plant Patent
Kobayashi

(10) Patent No.: US PP13,313 P2
(45) Date of Patent: Dec. 3, 2002

(54) POINSETTIA PLANT NAMED 'ECKAHEARN'

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/968,316

(22) Filed: Sep. 30, 2001

(51) Int. Cl.[7] ..... A01H 5/00
(52) U.S. Cl. ..... Plt./307
(58) Field of Search ..... Plt./307

(56) References Cited

U.S. PATENT DOCUMENTS

PP11,200 P * 2/2000 Fruehwirth ..... Plt./307

OTHER PUBLICATIONS

UPOV ROM GTITM Computer Database, GTI Jouve Retrieval Software, 2002/02, citation(s) for 'Eckahearn'.*

* cited by examiner

*Primary Examiner*—Bruce R. Campell
*Assistant Examiner*—W C Baker
(74) *Attorney, Agent, or Firm*—C. A. Whealy

(57) ABSTRACT

A new and distinct cultivar of Poinsettia plant named 'Eckahearn', characterized by its inflorescences with bright red-colored flower bracts; dark green-colored leaves with red-colored petioles; uniform and mounded plant habit; early flowering; and excellent post-production longevity.

2 Drawing Sheets

BOTANICAL CLASSIFICATION

*Euphorbia pulcherrima.*

BACKGROUND OF THE INVENTION

The present Invention relates to a new and distinct cultivar of Poinsettia plant, botanically known as *Euphorbia pulcherrima* Willd., and hereinafter referred to by the name 'Eckahearn'.

The new Poinsettia a product of a planned breeding program conducted by the Inventor in Encinitas, Calif. The objective of the breeding program is to create new Poinsettia cultivars having flower bracts with desirable colors, uniform plant habit and excellent post-production longevity.

The new Poinsettia is a naturally-occurring whole plant mutation of a unnamed proprietary induced mutation, not patented, that originated by exposing unrooted cuttings of the *Euphorbia pulcherrima* Willd. cultivar Eckabish, disclosed in U.S. Plant Pat. No. 11,200, to gamma radiation. The new Poinsettia was discovered and selected by the Inventor as a single plant within a population of plants of the irradiated selection on or about Aug. 19, 1998, in a controlled environment in Encinitas, Calif.

Asexual reproduction of the new Poinsettia by terminal cuttings taken at Encinitas, Calif., since October, 1998, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckahearn'. These characteristics in combination distinguish 'Eckahearn' as a new and distinct cultivar:

1. Inflorescences with bright red-colored flower bracts.
2. Dark green-colored leaves with red-colored petioles.

3. Uniform and mounded plant habit.
4. Early flowering, natural season flower maturity date is November 26 for plants grown in Encinitas, Calif.; response time, about 8.5 weeks.
5. Excellent post-production longevity.

Plants of the new Poinsettia are most similar to plants of the cultivar Eckabish. In side-by-side comparisons conducted in Encinitas, Calif., plants of the new Poinsettia differed primarily from plants of the cultivar Eckabish in the following characteristics:

1. Plants of the new Poinsettia were slightly taller, but not as wide as plants of the cultivar Eckabish.
2. Plants of the new Poinsettia had longer leaves than plants of the cultivar Eckabish.
3. Leaves of plants of the new Poinsettia had red-colored veins on the lower surface whereas leaves of plants of the cultivar Eckabish had green-colored veins on the lower surface.
4. Flower bract color of plants of the new Poinsettia was darker red than flower bract color of plants of the cultivar Eckabish.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of a typical flowering plant of 'Eckahearn' grown in a 16.5-cm container.

The photograph at the top of the second sheet comprises a top perspective view of a typical floweirng plant of 'Eckahearn'.

The photograph at the bottom of the second sheet is a close-up view of typical leaves, developing bracts and fully developed flower bracts of 'Eckabish' (top) and 'Eckahearn' (bottom).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the winter under commercial practice in a polyethylene-covered greenhouse with day temperatures about 24° C., night temperatures about 19° C., and light levels about 4,000 foot-candles. Single plants were grown in 16.5-cm pots and pinched once. Plants were flowered under natural season short day/long night conditions. Plants were about 17.5 weeks from unrooted cuttings when the photographs and the detailed botanical description were taken.

In the following description, color references are made to The Royal Horticultural Society Colour Chart except where general terms of ordinary dictionary significance are used.

Botanical classification:

*Euphorbia pulcherrima* Willd. cultivar Eckahearn.

Parentage: Naturally-occurring whole plant mutation of a unnamed proprietary *Euphorbia pulcherrima* Willd. induced mutation, not patented.

Propagation:

*Type cutting.*—Terminal cuttings.

*Time to initiate roots.*—About 10 days at 20 to 22° C.

*Time to develop roots.*—About 28 days at 20 to 22° C.

*Root description.*—Thick, fibrous and freely-branching.

Plant description:

*Plant form.*—Inverted triangle, top of plant rounded and mounding.

*Growth habit.*—Upright and uniform plant habit. Moderate vigor.

*Plant height.*—About 30 cm.

*Plant diameter or spread.*—About 39 cm.

*Lateral branch description.*—Quantity: About seven lateral branches develop after pinching. Length: About 26.5 cm. Diameter: About 7 mm. Internode length: About 3 cm. Color: 146A, occasionally overlain with anthocyanin, 59B.

*Foliage description.*—Arrangement: Alternate, single. Quantity of leaves per lateral branch: About 8. Length: About 11.75 cm. Width: About 8 cm. Shape: Mostly elliptic with irregular lobing. Apex: Acuminate. Base: Acute. Margin: Entire with irregular lobing. Venation pattern: Pinnate. Texture, upper and lower surfaces: Glabrous. Surface: Mostly flat, some undulation. Color: Young and fully expanded foliage, upper surface: Darker than 147A. Young and fully expanded foliage, lower surface: 147A. Venation, upper surface: 147C. Venation, lower surface: 59B to 59C. Petiole: Length: About 6.5 cm. Diameter: About 2 mm. Color: 59A.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under long nyctoperiod conditions. Response time, about 8.5 weeks; natural season flower maturity date is November 26 for plants grown in Encinitas, Calif.

*Post-production longevity.*—Plants of the new Poinsettia maintain good substance and bract color for about four weeks under interior conditions.

*Quantity of inflorescences per plant.*—One per lateral branch, about seven.

*Inflorescence size.*—Diameter: About 28 cm. Height (depth): About 5 to 8 cm.

*Flower bracts.*—Quantity: About 20 bracts per inflorescence. Length, largest bracts: About 12 cm. Width, largest bracts: About 8 cm. Shape: Mostly elliptic with irregular lobing. Apex: Acuminate. Base: Acute. Margin: Entire with irregular lobing. Texture, upper and lower surfaces: Glabrous, velvety. Surface: Mostly flat, some undulation. Orientation: Initially upright to drooping. Color: Developing or transitional bracts, upper surface: Irregular and random areas of 45B and darker than 147A, then becoming mostly 45B. Developing or transitional bracts, lower surface: Irregular and random areas of 46C and 147A, then becoming mostly 46C. Fully developed bracts, upper surface: 45B; color does not fade with subsequent development. Fully developed bracts, lower surface: 46B to 46C. Venation, upper and lower surfaces: Same as ground color. Bract petiole: Length: About 4 cm. Diameter: About 2 mm. Color: 60A.

*Cyathia.*—Quantity: About 16 per corymb. Diameter of cyathia cluster: About 2.5 by 3 cm. Length: About 1 cm. Width: About 7 mm. Shape: Ovoid. Color, immature and mature: 144A to 144B. Peduncle: Length: About 2 mm. Diameter: Less than 1 mm. Aspect: Strong, erect. Color: 144B. Stamens: Stamen number: About 15 per cyathium. Anther shape: Oval. Anther length: Less than 1 mm. Anther color: 59A. Amount of pollen: Scarce. Pollen color: 7A. Pistils: None observed. Nectary number: One per cyathia. Nectary color: 23A.

Disease/pest resistance: Resistance to pathogens and pests common to Poinsettias has not been observed on plants grown under commercial conditions.

It is claimed:

1. A new and distinct cultivar of Poinsettia plant named 'Eckahearn', as illustrated and described.

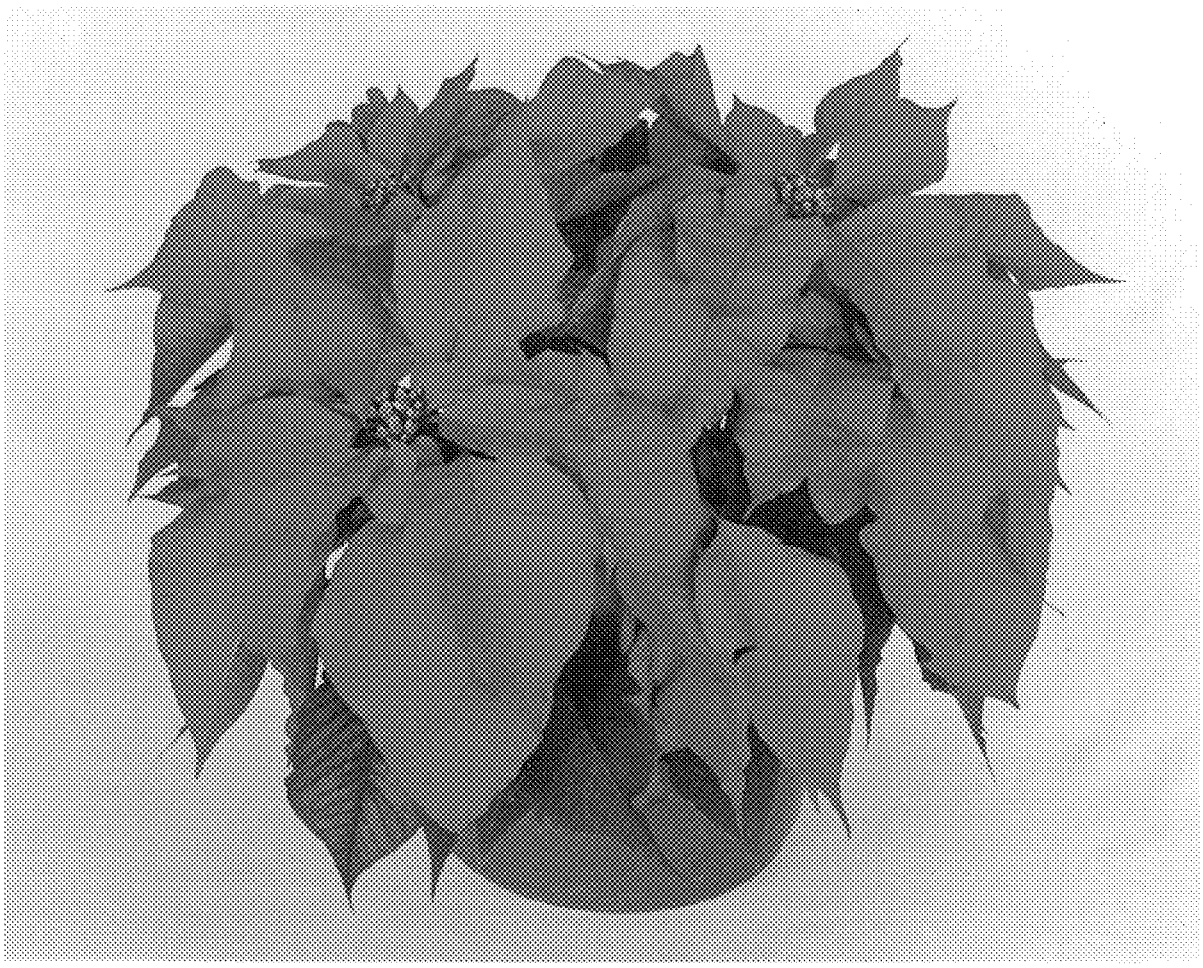

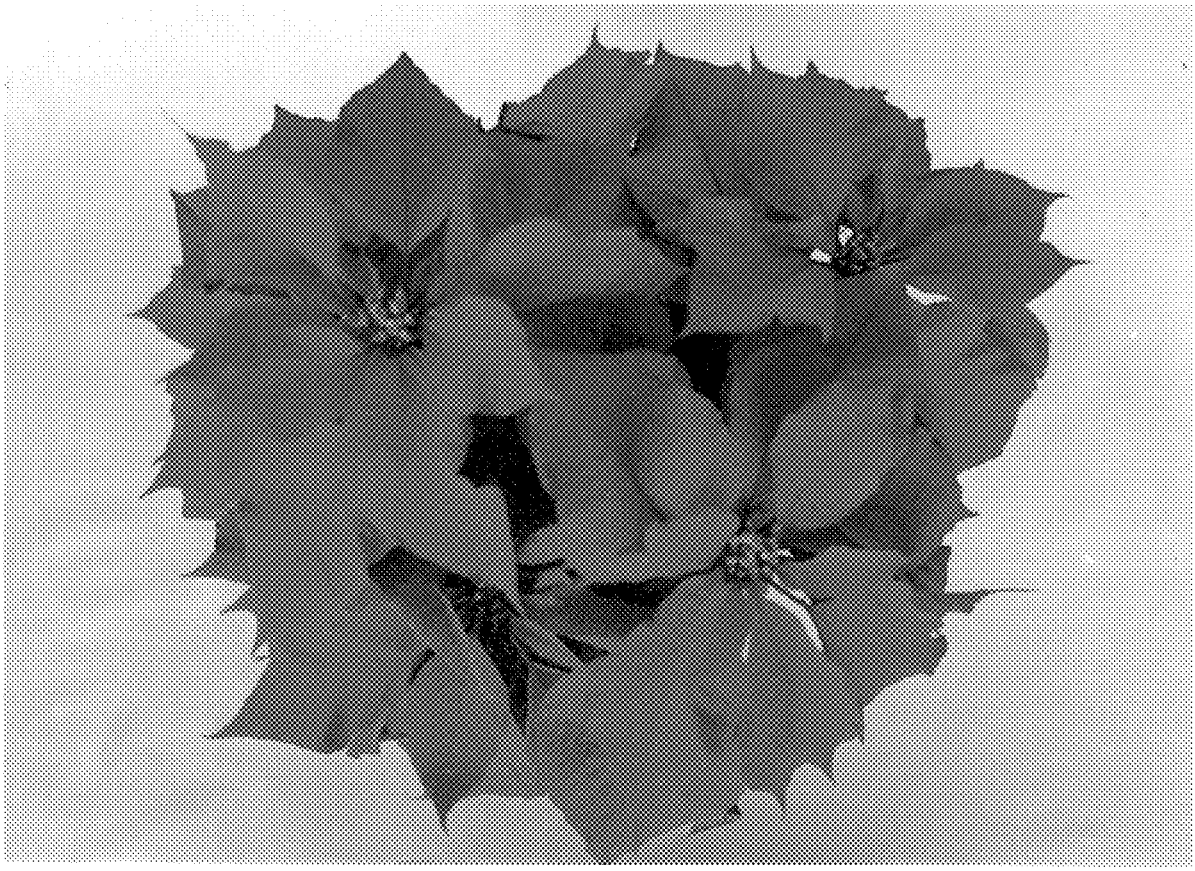
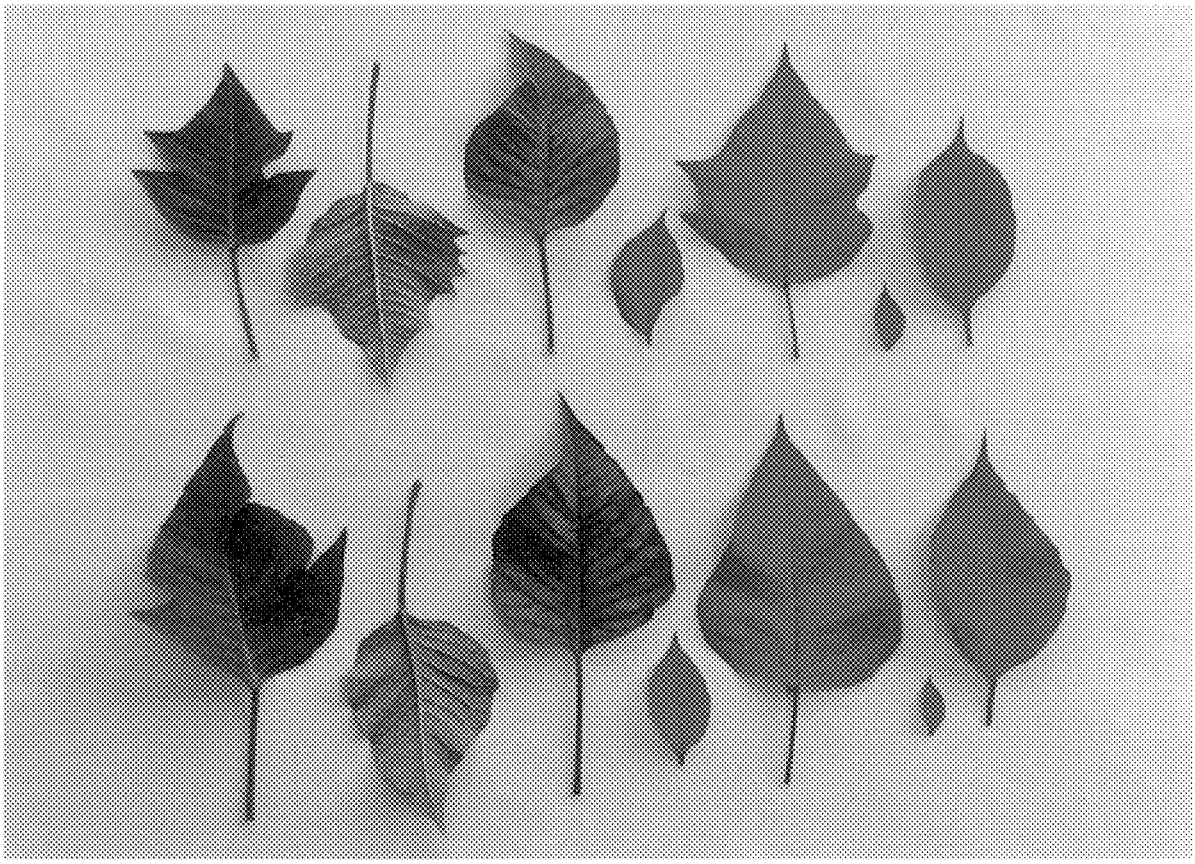

* * * * *